US012674736B2

(12) United States Patent
DeHart et al.

(10) Patent No.: US 12,674,736 B2
(45) Date of Patent: Jul. 7, 2026

(54) TECHNIQUE AND TEST FIXTURE TO CONDUCT FLOW TESTING SIMULATING A GRAVEL PACK IN A LAB ENVIRONMENT AT DOWNHOLE CONDITIONS

(71) Applicant: Halliburton Energy Services, Inc., Houston, TX (US)

(72) Inventors: Rory Jude DeHart, Burleson, TX (US); John Norris Smith, Burleson, TX (US); Aaron Thomas Lafleur, Joshua, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 1641 days.

(21) Appl. No.: 17/054,014

(22) PCT Filed: May 24, 2019

(86) PCT No.: PCT/US2019/033939
§ 371 (c)(1),
(2) Date: Nov. 9, 2020

(87) PCT Pub. No.: WO2019/231845
PCT Pub. Date: Dec. 5, 2019

(65) Prior Publication Data
US 2026/0023005 A1      Jan. 22, 2026

Related U.S. Application Data

(60) Provisional application No. 62/679,135, filed on Jun. 1, 2018.

(51) Int. Cl.
*G01N 15/08* (2006.01)
*G01N 33/24* (2006.01)

(52) U.S. Cl.
CPC ......... *G01N 15/0826* (2013.01); *G01N 33/24* (2013.01)

(58) Field of Classification Search
CPC .... G01N 15/00; G01N 15/08; G01N 15/0826; G01N 33/24
See application file for complete search history.

(56) References Cited

U.S. PATENT DOCUMENTS 7,861,609 B2 * 1/2011 Haggerty ............... G01N 33/24
73/866.5
8,312,920 B2 11/2012 Tehrani et al.
(Continued)

FOREIGN PATENT DOCUMENTS

CN 104407099 A 3/2015
CN 105074456 A 11/2015
(Continued)

*Primary Examiner* — Nguyen Q. Ha
(74) *Attorney, Agent, or Firm* — John Wustenberg; Parker Justiss, P.C.

(57) ABSTRACT

Provided is a test gravel pack assembly. The test gravel pack assembly, in one instance, includes a housing having first and second opposing surfaces, the first and second opposing surfaces defining a thickness that simulates a desired downhole gravel pack thickness. In this instance, the test gravel pack assembly includes an opening extending entirely through the housing from the first surface to the second surface, the opening having a diameter that simulates a desired downhole wellbore casing perforation diameter, and a proppant screen coupled proximate the first opposing surface and over the opening.

19 Claims, 8 Drawing Sheets

(56) References Cited

U.S. PATENT DOCUMENTS

| | | | |
|---|---|---|---|
| 8,950,252 B2 | 2/2015 | Haggerty | |
| 9,070,049 B2 | 6/2015 | Fredrich et al. | |
| 9,279,904 B2 * | 3/2016 | Brooks | G01V 11/002 |
| 10,613,239 B2 * | 4/2020 | Manning | E21B 43/1185 |
| 2008/0236891 A1 | 10/2008 | Huynh et al. | |
| 2012/0211089 A1 * | 8/2012 | Piri | G01N 15/082 |
| | | | 137/565.13 |
| 2014/0319080 A1 | 10/2014 | Kaarigstad et al. | |
| 2016/0290909 A1 | 10/2016 | Burks et al. | |
| 2016/0334322 A1 * | 11/2016 | Ramakrishnan | G01N 15/0826 |
| 2021/0324719 A1 * | 10/2021 | Jin | G01N 15/0826 |

FOREIGN PATENT DOCUMENTS

| | | |
|---|---|---|
| CN | 104777272 B | 3/2017 |
| CN | 107860569 A | 3/2018 |
| WO | 2019231845 A1 | 12/2019 |

* cited by examiner

300
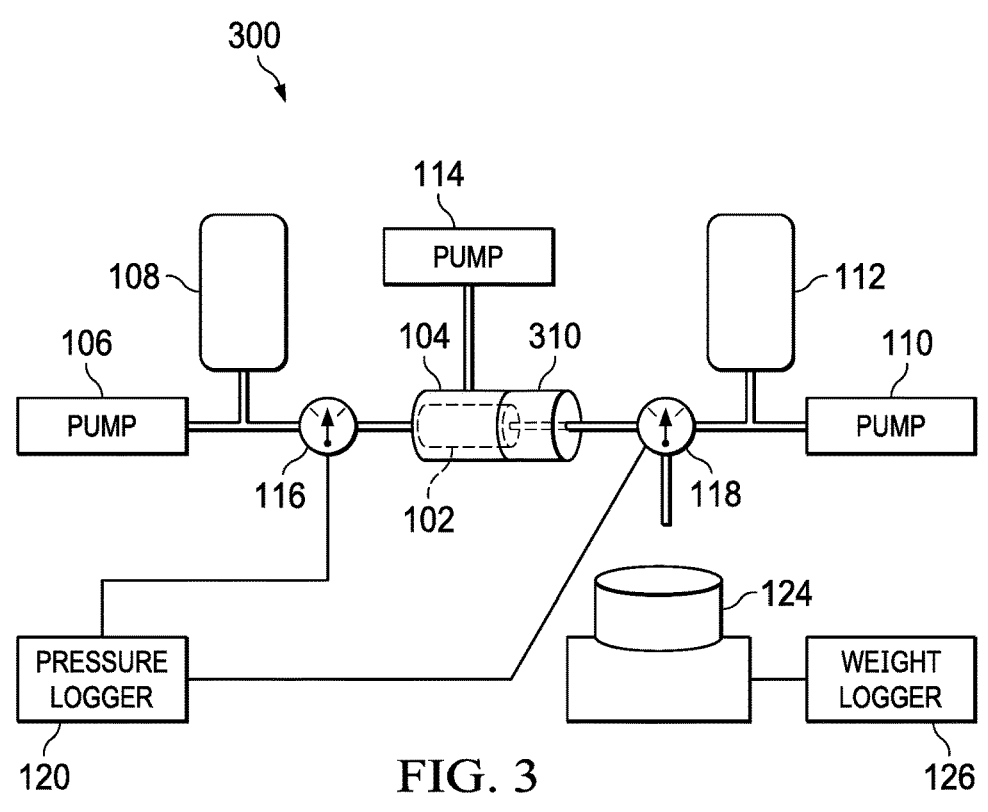
108
114
112
106
104　310
110
PUMP
PUMP
PUMP
116
102
118
PRESSURE LOGGER
124
WEIGHT LOGGER
120
FIG. 3
126
600
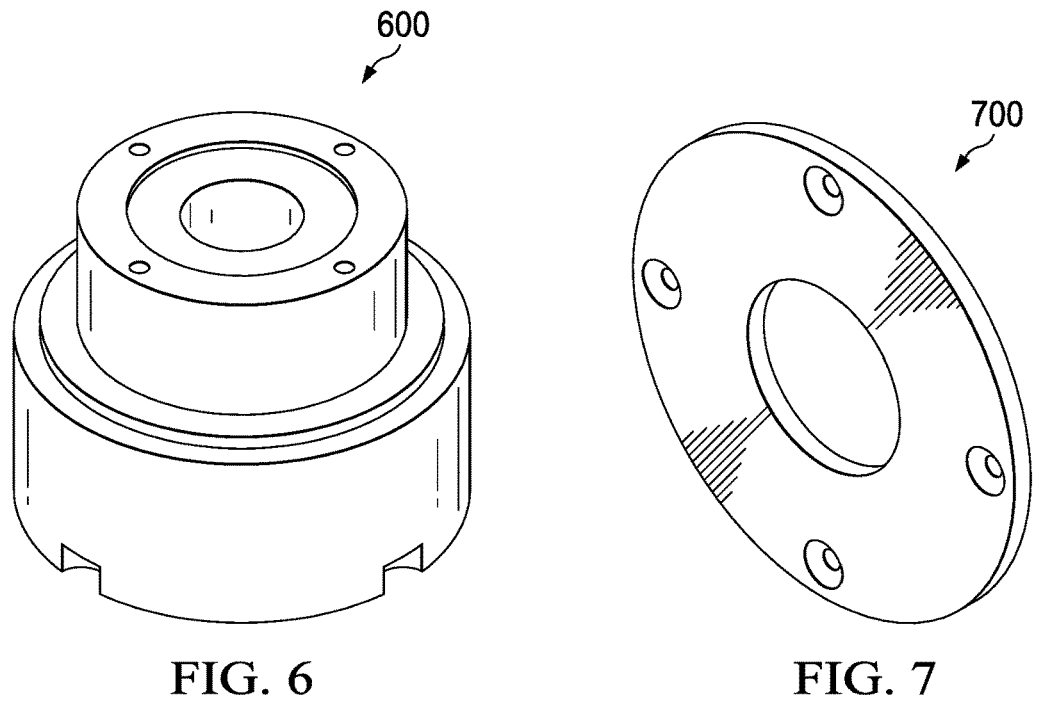
700
FIG. 6　　　　　　　FIG. 7

400C

460

C

490

410

499

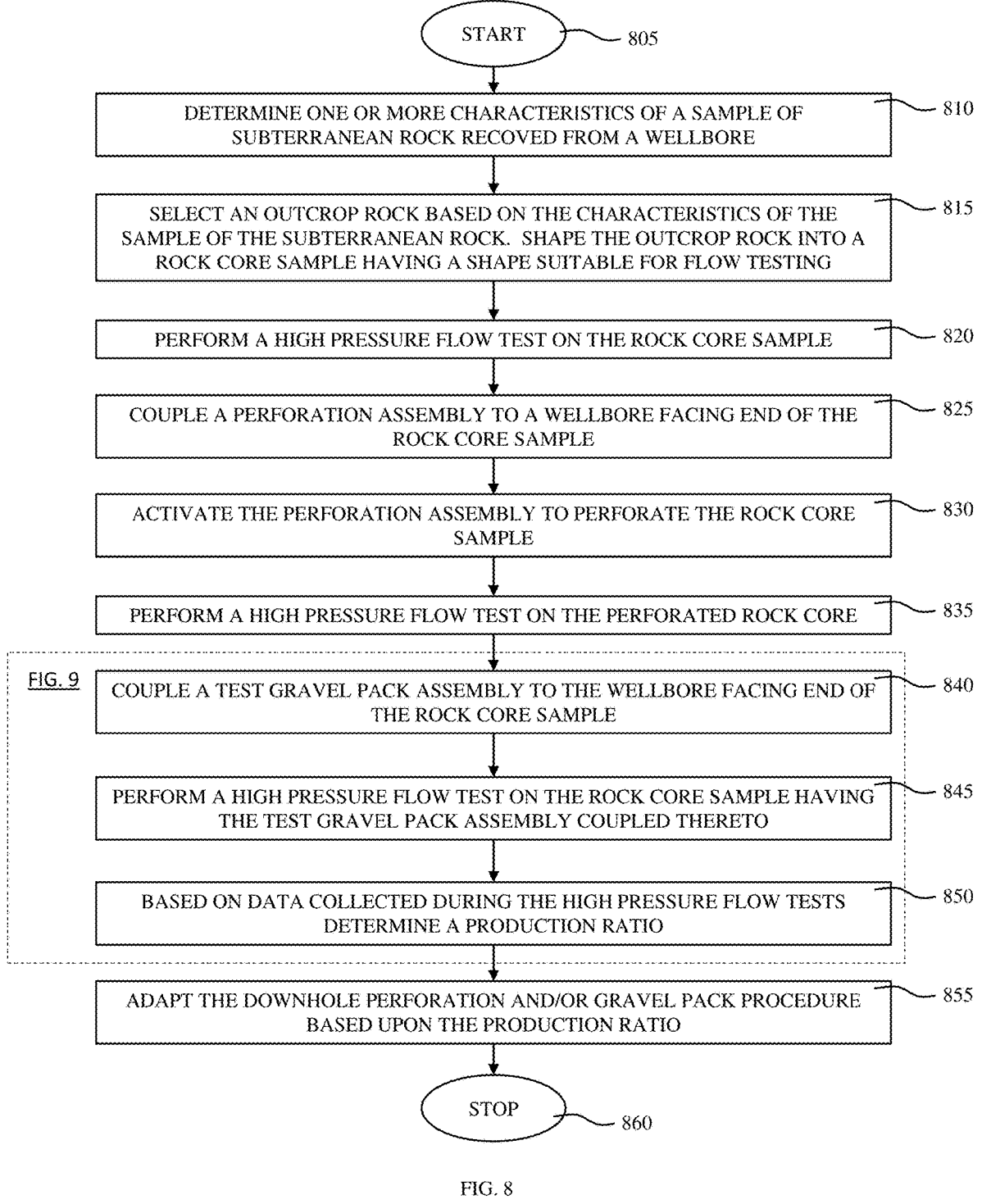

START — 805

DETERMINE ONE OR MORE CHARACTERISTICS OF A SAMPLE OF SUBTERRANEAN ROCK RECOVED FROM A WELLBORE — 810

SELECT AN OUTCROP ROCK BASED ON THE CHARACTERISTICS OF THE SAMPLE OF THE SUBTERRANEAN ROCK. SHAPE THE OUTCROP ROCK INTO A ROCK CORE SAMPLE HAVING A SHAPE SUITABLE FOR FLOW TESTING — 815

PERFORM A HIGH PRESSURE FLOW TEST ON THE ROCK CORE SAMPLE — 820

COUPLE A PERFORATION ASSEMBLY TO A WELLBORE FACING END OF THE ROCK CORE SAMPLE — 825

ACTIVATE THE PERFORATION ASSEMBLY TO PERFORATE THE ROCK CORE SAMPLE — 830

PERFORM A HIGH PRESSURE FLOW TEST ON THE PERFORATED ROCK CORE — 835

FIG. 9

COUPLE A TEST GRAVEL PACK ASSEMBLY TO THE WELLBORE FACING END OF THE ROCK CORE SAMPLE — 840

PERFORM A HIGH PRESSURE FLOW TEST ON THE ROCK CORE SAMPLE HAVING THE TEST GRAVEL PACK ASSEMBLY COUPLED THERETO — 845

BASED ON DATA COLLECTED DURING THE HIGH PRESSURE FLOW TESTS DETERMINE A PRODUCTION RATIO — 850

ADAPT THE DOWNHOLE PERFORATION AND/OR GRAVEL PACK PROCEDURE BASED UPON THE PRODUCTION RATIO — 855

STOP — 860

FIG. 8

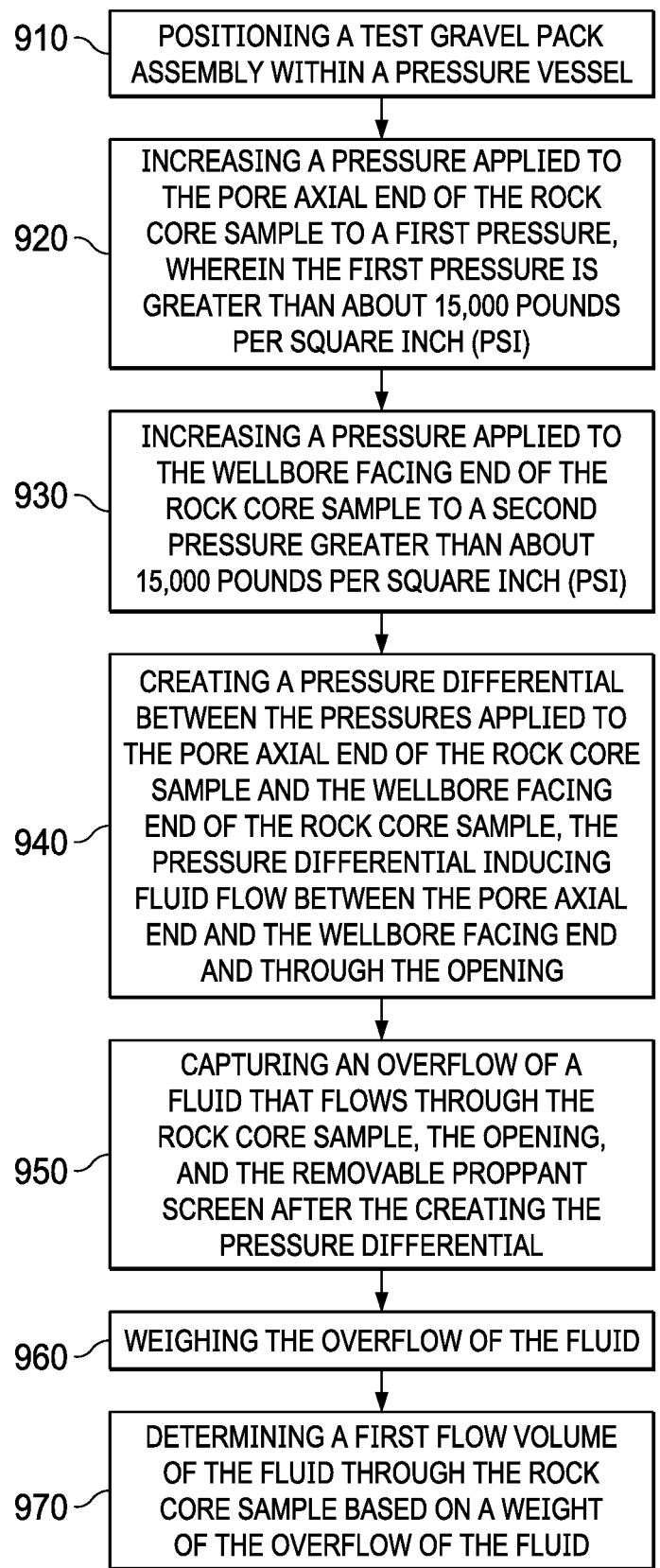

910 — POSITIONING A TEST GRAVEL PACK ASSEMBLY WITHIN A PRESSURE VESSEL

920 — INCREASING A PRESSURE APPLIED TO THE PORE AXIAL END OF THE ROCK CORE SAMPLE TO A FIRST PRESSURE, WHEREIN THE FIRST PRESSURE IS GREATER THAN ABOUT 15,000 POUNDS PER SQUARE INCH (PSI)

930 — INCREASING A PRESSURE APPLIED TO THE WELLBORE FACING END OF THE ROCK CORE SAMPLE TO A SECOND PRESSURE GREATER THAN ABOUT 15,000 POUNDS PER SQUARE INCH (PSI)

940 — CREATING A PRESSURE DIFFERENTIAL BETWEEN THE PRESSURES APPLIED TO THE PORE AXIAL END OF THE ROCK CORE SAMPLE AND THE WELLBORE FACING END OF THE ROCK CORE SAMPLE, THE PRESSURE DIFFERENTIAL INDUCING FLUID FLOW BETWEEN THE PORE AXIAL END AND THE WELLBORE FACING END AND THROUGH THE OPENING

950 — CAPTURING AN OVERFLOW OF A FLUID THAT FLOWS THROUGH THE ROCK CORE SAMPLE, THE OPENING, AND THE REMOVABLE PROPPANT SCREEN AFTER THE CREATING THE PRESSURE DIFFERENTIAL

960 — WEIGHING THE OVERFLOW OF THE FLUID

970 — DETERMINING A FIRST FLOW VOLUME OF THE FLUID THROUGH THE ROCK CORE SAMPLE BASED ON A WEIGHT OF THE OVERFLOW OF THE FLUID

FIG. 9

TECHNIQUE AND TEST FIXTURE TO CONDUCT FLOW TESTING SIMULATING A GRAVEL PACK IN A LAB ENVIRONMENT AT DOWNHOLE CONDITIONS

CROSS-REFERENCE TO RELATED APPLICATION

This application is the National Stage of, and therefore claims the benefit of, International Application No. PCT/US2019/033939 filed on May 24, 2019, entitled "TECHNIQUE AND TEST FIXTURE TO CONDUCT FLOW TESTING SIMULATING A GRAVEL PACK IN A LAB ENVIRONMENT AT DOWNHOLE CONDITIONS," which was published in English under International Publication Number WO 2019/231845 on Dec. 5, 2019, and has a priority date of Jun. 1, 2018, based on U.S. application 62/679,135. Both of the above applications are commonly assigned with this National Stage application and are incorporated herein by reference in their entirety.

BACKGROUND

In order to design the perforation tool and/or a downhole perforation procedure, one or more rock cores that are considered to be representative of the subterranean formation to be perforated may be tested in a test laboratory uphole to determine some parameters of the subterranean formation and/or interactions between the explosive charges and the subterranean formation. The evaluations of test results may be used in designing the perforation tool and/or the downhole perforation procedure. What is needed in the art is an improved method and test fixture representative rock cores.

BRIEF DESCRIPTION

Reference is now made to the following descriptions taken in conjunction with the accompanying drawings, in which:

FIGS. 1-3 illustrate various embodiments of a rock core flow test system manufactured and designed according to the disclosure;

FIGS. 6 and 7 illustrate a gravel pack simulation lab fixture and a cap, respectively, manufactured and designed according to the disclosure;

FIG. 8 illustrates a method of performing a rock core flow performance test in accordance with one embodiment of the disclosure; and FIG. 9 illustrates a process flow, which expands steps 840, 850 and 860 of FIG. 8 into sub-steps.

DETAILED DESCRIPTION

Figure 1:
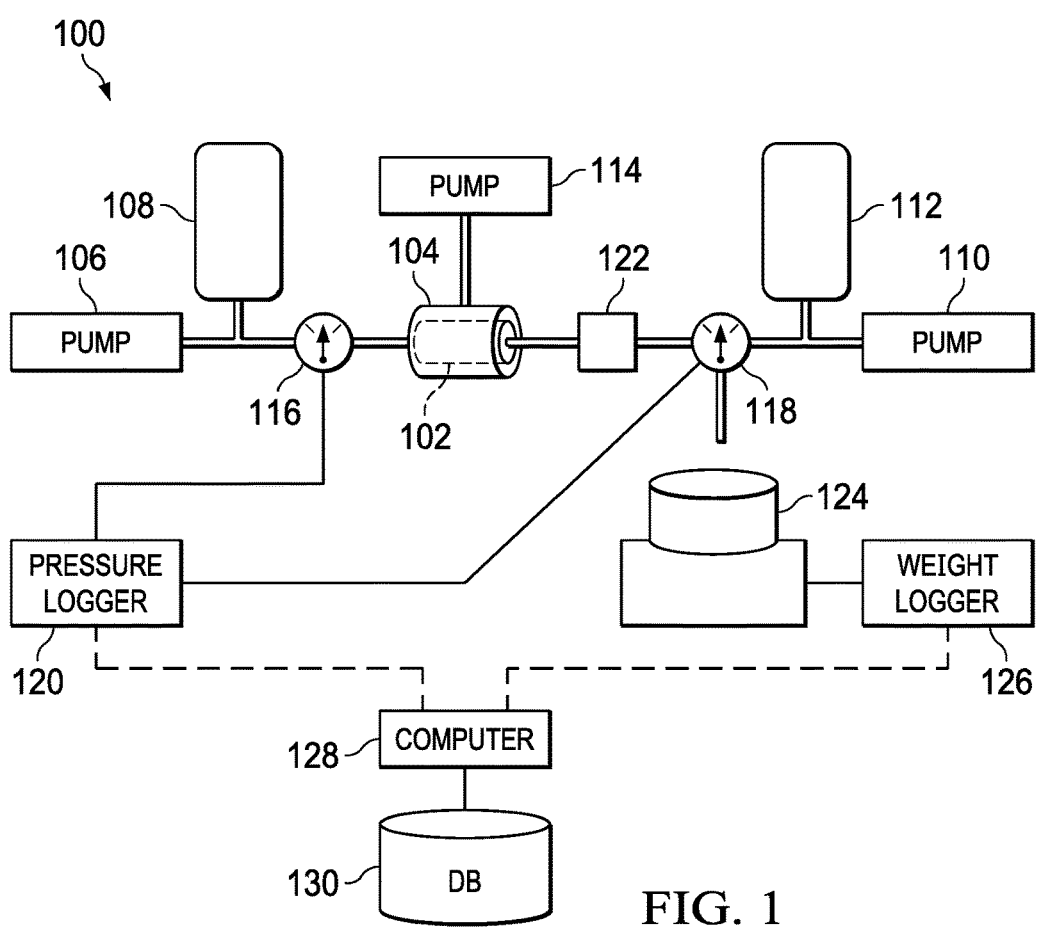

It should be understood at the outset that although illustrative implementations of one or more embodiments are discussed below, the disclosed systems and methods may be implemented using any number of techniques, whether currently known or in existence. The disclosure should in no way be limited to the illustrative implementations, drawings, and techniques shown below, but may be modified within the scope of the appended claims along with their full scope of equivalents.

Unless otherwise specified, any use of any form of the terms "connect," "engage" "couple" "attach," or any other term describing an interaction between elements is not meant to limit the interaction to direct interaction between the elements and may also include indirect interaction between the elements described. Reference to up or down will be made for purposes of description with "up," "upper," "upward," or "upstream" meaning toward the surface of the wellbore and with "down," "lower," "downward, or "downstream" meaning toward the terminal end of the well, regardless of the wellbore orientation. The term "zone" or "pay zone" as used herein refers to separate parts of the wellbore designated for treatment or production and may refer to an entire hydrocarbon formation or separate portions of a single formation, such as horizontally and/or vertically spaced portions of the same formation. The various characteristics mentioned above, as well as other features and characteristics described in more detail below, will be readily apparent to those skilled in the art with the aid of this disclosure upon reading the following detailed description of the embodiments, and by referring to the accompanying drawings.

Testing of rock cores may be conducted to evaluate and to adjust perforation gun design parameters and perforation procedure parameters. Testing may be conducted based on American Petroleum Institute (API) reference procedure 19B (API RP 19B), Recommended Practices for Evaluation of Well Perforators, First Edition, November 2000. Testing is typically performed on a rock core that is considered to be representative of the subterranean formation. For example, rock cuttings from a subterranean formation retrieved from the wellbore to be perforated are captured and analyzed to determine characteristics of the rock of the subterranean formation. An outcrop rock is selected based on the similarity of its characteristics to the characteristics of the rock cuttings from the subterranean formation. The outcrop rock is trimmed to a form suitable for core testing, for example a circular cylinder form about 18 centimeters (e.g., a little over 7 inches) in diameter and about 70 centimeters (e.g., a little over 27 inches) in axial length, in one example. The length of the rock core sample may be a different length, as discussed in further detail below, depending on the perforation tunnel depth expected to be produced by the perforation charge. In some cases, a rock core sample may be extracted from the wellbore and used in rock core testing, but such core samples are expensive to obtain and are less and less frequently available.

The present disclosure contemplates performing at least some of the core testing using high pressure conditions that may be seen in some downhole environments. This high pressure core testing presents design challenges. In one or more embodiments, the rock core sample is flow tested under high pressure without perforation; during a simulated perforation event, the rock core sample is flow tested under high pressure after perforation; and/or under a simulated gravel pack scenario; and a metric is calculated relating the various flows to determine if the perforation improved the flow, and the effect of the gravel pack on the flow characteristics. If the perforation did not improve the flow, or the gravel pack has a negative effect on the flow characteristics, the perforation gun design or gravel pack procedure may be adapted accordingly. The metric can also be used to compare among a plurality of different perforation gun designs to select the perforation gun design that performs best in the rock core test. In one or more embodiments, evaluation of flow results are based on pressure sensed at a well bore axial face of the rock core rather than directly sensing fluid flow rate.

The rock core may be placed in a containment or pressure vessel that is sealed at one end, for example by a fast opening flow control device such as a rupture disc. The rock core may be disposed within a sleeve or bladder and an external surface of the sleeve or bladder may be subjected in certain embodiments to a high overburden pressure or confining pressure along at least a portion of its surface (e.g., along its radial surface), for example an overburden pressure greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI. The application of the pressure to the sleeve or bladder may be referred to as an indirect pressure based on the lack of any direct contact between the fluid exerting the overburden pressure and the rock core. The over burden pressure or confining pressure may be viewed as simulating the pressure experienced in the downhole environment.

A subterranean formation axial end or pore axial end of the rock core may be subjected to a fluid having a high pressure greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI, but in one embodiment less than the overburden pressure or confining pressure. In some contexts, the pressure applied to the pore axial end of the rock core may be referred to as the flow pressure based on the direct contact between the fluid and the rock core.

The wellbore facing end of the fast opening flow control device may be subjected to a high pressure greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI, but in one embodiment less than the overburden pressure. The pressure on the pore axial end of the rock core and the pressure on the wellbore facing end of the fast opening flow control device may be increased in unison so that they remain substantially equal up to a first pressure.

In one embodiment, the first pressure is maintained at the pore axial end of the rock core while the pressure on the wellbore facing side of the fast opening flow control device is decreased until a pressure difference between the pressure on the pore axial end of the rock core and the pressure on the wellbore facing end of the fast opening flow control device exceed a predefined threshold, for example a pressure differential of about 2,000 PSI. It is understood that when the fast opening flow control device is closed (hence no fluid flows through the rock core sample), the pressure applied to the pore axial end of the rock core is equalized across the rock core sample, and the pressure applied to the pore axial end of the rock core is equal to the pressure applied to a core facing side of the fast opening flow control device. As the pressure differential exceeds the predefined threshold, the fast opening flow control device opens quickly, for example, the rupture disc ruptures. The pressure on the well bore facing side of the fast opening flow control device when the device activates or opens may be referred to as a second pressure. The second pressure is less than the first pressure. After the fast opening flow control device activates, the rock core sample experiences a flow, and the pressure at the wellbore facing side of the fast opening flow control device drops from the second pressure to a third pressure over a first time interval. In combination with the present disclosure, the first pressure, the second pressure, and the third pressure may be selected by one skilled in the art. In practice, the selection of the first pressure, the second pressure, and the third pressure may be based, at least in part, on available or conveniently manufactured fast opening flow control devices. The pressures may also be selected at least in part to simulate downhole conditions as nearly as is practicable.

After the non-perforated rock core test, a perforation may be formed in the rock core by coupling a perforation assembly (e.g., including an explosive charge) thereto. The explosive charge may, in certain embodiments, comprise a shaped explosive, a charge liner, and a metal layer that models a tool body of a perforation gun proximate to the explosive charge.

The rock core and this perforation assembly may then be placed in the vessel. In this situation, the wellbore facing axial end of the rock core is sealed by the perforation assembly. The rock core may again be indirectly exposed to high overburden pressure along at least a portion of its radial surface, for example an overburden pressure greater than about 5,000 pounds per square inch (PSI), 10,000 PSI, 15,000 PSI, 20,000 PSI, 25,000 PSI, 30.000 PSI, 35,000 PSI, 40,000 PSI, 45,000 PSI, or 50,000 PSI. The pore axial end of the rock core may be subjected to a high pressure greater than about 5,000 pounds per square inch (PSI), 10,000 PSI, 15,000 PSI, 20,000 PSI, 25,000 PSI, 30,000 PSI, 35,000 PSI, 40,000 PSI, 45,000 PSI, or 50,000 PSI, but less than the overburden pressure.

The wellbore facing end of the perforation assembly may be directly subjected to a high pressure greater than about 5,000 pounds per square inch (PSI), 10,000 PSI, 15,000 PSI, 20,000 PSI, 25,000 PSI, 30,000 PSI, 35,000 PSI, 40,000 PSI, 45,000 PSI, or 50,000 PSI, but less than the overburden pressure. The well bore facing end of the perforation assembly may be directly subjected to a pressure substantially equal to the pressure at which the fast opening flow control device described above opened, for example to the second pressure described above.

The explosive charge may then be fired, and the explosion creates a perforated area in the rock core sample. As is known by one skilled in the art, the length of the rock core sample is sized to avoid the perforated area penetrating all the way through the rock core. The API RP 19B Recommended Practices for Evaluation of Well Perforators, identified above, recommends that the tunnel extend no further than a distance equal to the diameter from the pore end of the rock core sample. For example, if the rock core sample is 7 inches in diameter and 28 inches long, the tunnel caused by the explosion should penetrate no further than 21 inches into the rock core (and hence 7 inches from the pore end of the rock core sample). The rock core sample may be examined after the explosion and after the transient pressure test to determine if this recommendation has been satisfied, for example, a sonogram of the rock core sample after the explosion may be made using an ultrasonic analysis tool. If the explosion penetrates excessively into the rock core, a longer rock core sample may be formed and one or more of the tests may be repeated with the longer rock core sample.

After perforation, the rock core experiences a flow, and the pressure at the wellbore facing axial end of the rock core drops from the second pressure to the third pressure over a second time interval. The first and second time intervals can be compared to determine a production ratio that promotes an evaluation of the effectiveness of the explosive charge design for use with the rock core sample. In one or more embodiments, the volumetric flow of fluid through the rock core sample under high pressure may be determined by capturing overflow of fluids and weighing the fluid. Under the high pressure conditions of the rock core sample testing the fluid may experience compression. Accordingly, the volumetric flow of fluid through the rock core sample may be determined by determining the uncompressed volume of the fluid based on the measured weight and then converting this uncompressed volume to a compressed volume based on known or determinable compressibility relationships of the subject fluid. Standard flow rate sensors may not be practicable in the high pressure test environment taught by the present disclosure, for example testing in an environment with pressures greater than about 25,000 PSI. In one or more embodiments, the rock core sample is flowed with odorless mineral spirits (ODM), while in other embodiments a different fluid may be flowed in the rock core sample. The description above describes fluid flowing from the pore axial end to the wellbore axial end of the rock core, with substantially no flow across the radial axial surface of the rock core sample, as might be relevant in a production well scenario. Nevertheless, in one or more other embodiments, the core test procedure may be modified and fluid may flow from the wellbore axial end to the pore axial end of the rock core sample, with substantially no flow across the radial axial surface of the rock core, as might be relevant in an injection well scenario.

Subsequent to testing the rock core sample having the perforation, the rock core sample having the perforation may be removed from the pressure chamber, and a gravel pack simulation lab fixture may be coupled thereto. The gravel pack simulation lab fixture, in accordance with one embodiment of the disclosure, comprises a housing having a two opposing surfaces, the two opposing surfaces including an opening extending there between. With one of the surfaces of the gravel pack simulation lab fixture coupled to the rock core sample having the perforation, proppant may be placed within the opening from the opposing surface, substantially filling the opening, and in certain embodiments packing into the perforated area. Thereafter, a screen assembly may be coupled to the exposed opposing surface over the opening, thus retaining the proppant within the gravel pack simulation lab fixture. At this stage, the rock core sample having the perforation and gravel pack simulation lab fixture attached thereto simulates a downhole gravel pack scenario.

The rock core sample having the gravel pack simulation lab fixture attached thereto, may then be placed within the pressure chamber and re-subjected to the pressure tests previously run on the rock core sample having the perforation. Accordingly, similar test results as were obtained on the rock core sample having the perforation may be obtained on the rock core having the gravel pack simulation lab fixture coupled thereto. In certain embodiments, it is not necessary, or may even be detrimental, to conduct the pressure tests on the rock core sample having only the perforation therein, and thus this step is omitted. Accordingly, the process would not conduct the pressure tests on the rock core sample only having the perforation, and would jump directly from the pressure test without the perforation to the pressure test with the gravel pack simulation lab fixture attached to the rock core sample having the perforation.

It is understood that in some embodiments, the pressure test that employs a fast opening flow control device may be performed without the pressure test that explodes an explosive charge. In some embodiments, the pressure test that explodes the explosive charge may be performed without the pressure test that employs the fast opening flow control device. In some embodiments, the pressure test that simulates the gravel pack scenario may be performed without the pressure test that employs the fast opening flow control device or the pressure test that explodes the explosive charge.

Turning now to FIG. 1, a rock core flow test system 100 is described. Testing a rock core sample may be referred to simply as core testing. In one or more embodiments, the system 100 comprises a rock core sample 102, a containment vessel 104, a first pump 106, a first high pressure accumulator 108, a second pump 110, a second high pressure accumulator 112, and a third pump 114, among other elements. The system 100 may further comprise a first pressure sensor 116, a second pressure sensor 118, a high speed pressure logger 120, a fast opening high pressure flow control device 122, a scale 124, and a weight logger 126, again among other elements. In some contexts, the fast opening high pressure flow control device 122 may be referred to as a high speed high pressure flow control device. The pumps 106, 110, and 114 are capable of providing fluid at high pressure, for example fluid at pressures greater than about 5,000 pounds per square inch (PSI), 10,000 PSI, 15,000 PSI 20,000 PSI, 25,000 PSI, 30,000 PSI, 35,000 PSI, 40,000 PSI, 45,000 PSI, or 50,000 PSI. In one or more embodiments, the pumps 106, 110, and 114 may be capable of supplying fluid pressurized up to about 50,000 PSI. The pumps 106, 110, and 114 may be triplex type pumps, though, in other embodiments, a different type of pump may be employed.

It is understood that the system 100 may contain components and equipment not explicitly described herein. For example, a flow distributor (not shown) may be coupled between the rock core sample 102 and the first pump 106 and/or the first accumulator 108. High pressure piping may be used to couple components of the system 100 to each other. Check valves may be used to impose one-way flow directionality in some portions of the system 100. Pressure relief valves may be used to promote safety and/or to promote collecting fluid as an indication of fluid flow through the rock core sample 102.

The system 100 may promote maintaining a constant over burden pressure or confining pressure on the radial surface of the rock core sample 102 that is different from the pressure applied to the axial ends of the rock core sample 102, wherein fluid flow may occur across a pore axial end of the rock core sample 102 and fluid flow is substantially blocked across the radial surface of the rock core sample 102. In one or more embodiments, a sleeve or bladder surrounds the radial surface of the rock core sample 102 and prevents or attenuates fluid flow across the radial surface of the rock core sample 102. Pressure applied to the sleeve, e.g., overburden or confining pressure, is then applied to the radial surface of the rock core sample 102. Alternatively, in one or more embodiments, the system 100 may promote maintaining the same pressure on the pore axial end of the rock core sample 102 and on the radial surface of the rock core sample 102, wherein fluid flow may occur across both the pore axial end of the rock core sample 102 and across the radial surface of the rock core sample 102. In yet another alternative embodiment, the system 100 may promote sealing the pore axial end of the rock core sample 102 and applying pressure to the radial surface of the rock core sample 102 and flowing fluid across the radial surface of the rock core sample 102. In some contexts, the rock core sample 102 may be referred to as a core sample. In other contexts, however, the term core sample may be reserved to distinguish a rock core that has been extracted from the specific subterranean formation and the wellbore for which a perforation gun is to be designed. In some contexts, the containment vessel 104 may be referred to as a pressure vessel.

The high pressure accumulators 108, 112 receive in-flow of fluid that is resisted by a chamber of the accumulators that is filled with a compressible substance such as nitrogen gas. The high pressure accumulators 108, 112 act to maintain an operating pressure by delivering fluid flow and receiving fluid flow to maintain pressure through fluid flow demand transients. Accordingly, the high pressure accumulator 108 may be in fluid communication with the pore axial end of a rock core sample and the high pressure accumulator 112 may be in fluid communication with the wellbore facing end of the rock core sample. One skilled in the art can be expected to be familiar with the principle of operation of such accumulators. It is to be noted that the high pressure accumulators 108, 112 are designed, in certain embodiments, specifically for operating at high pressures above 25,000 PSI. The design characteristics of the high pressure accumulators 108, 112 that make them suitable for use in high pressure environments may include strength of the accumulator vessel, a shape of the accumulator vessel, and an initial pressure of the compressible substance contained by the accumulator. For example, in one or more embodiments, the accumulator vessel may have a substantially spherical shape.

The fast opening high pressure flow control device 122 is designed to open rapidly when a pressure differential across the component exceeds a predefined threshold. For example, the predefined threshold may be about 500 PSI, about 1000 PSI, about 2000 PSI, or some other pressure differential. One of ordinary skill in the art will appreciate that individual fast opening flow control devices may manifest some unit-to-unit variation without nullifying the value of the tests. For example, a specific instance of a fast opening high pressure flow control device 122 designed to open in response to a pressure differential exceeding 500 PSI may in fact open when the pressure differential exceeds 450 PSI or may not open until the pressure differential exceeds 550 PSI. Generally, such unit-to-unit variation can be tolerated or this variation may be accommodated by post-test analysis of test data. Alternatively, if the unit-to-unit variation experienced during a core test is excessive, the subject test results may be discarded and the core testing may be repeated.

It is understood that, in some embodiments, the fast opening high pressure flow control device 122 is designed for use in high pressure environments, for example, in environments with pressures greater than about 5,000 pounds per square inch (PSI), 10,000 PSI, 15,000 PSI, 20,000 PSI, 25,000 PSI, 30,000 PSI, 35,000 PSI, 40,000 PSI, 45,000 PSI, or 50,000 PSI. In some contexts, the fast opening high pressure flow control device 122 may be referred to as the high speed flow control device 122.

For purposes of the present disclosure, fast opening means that the subject flow control device is substantially fully opened after a period of time that is small relative to the time interval used to determine the production ratio. For example, in one or more embodiments, after the onset of the opening of the fast opening flow control device 122, the fast opening flow control device 122 is at least 80% fully open before 20% of the time interval used to determine the production ratio. Alternatively, in one or more embodiments, after the onset of the opening of the fast opening flow control device 122, the fast opening flow control device 122 is at least 80% fully open before 10% of the time interval used to determine the production ratio.

Alternatively, the fast opening flow control device 122 may be substantially open in less than about 500 milliseconds (mS), less than about 300 mS, less than about 10 mS, less than about 5 mS, less than about 1 mS, less than about 100 microseconds ($\mu$S), less than about 50 $\mu$S, less than about 10 $\mu$S, less than about 5 $\mu$S, or less than about 1 $\mu$S. In one or more embodiments, the fast opening flow control device 122 may be a rupture disc. In another embodiment, the fast opening flow control device 122 may be a valve that is held closed by a shear pin or shear disc that fails predictably at a predefined pressure differential across the fast opening flow control device 122 and after failure undergoes rapid opening in response to the forcing of the pressure differential and an associated fluid flow. In another embodiment, a different form of valve may be used to provide the fast opening flow control device 122.

The high speed pressure logger 120 receives indications of pressure from the first pressure sensor 116 and from the second pressure sensor 118, which are designed to measure changes in pressure in one or both of the first high pressure accumulator or the second high pressure accumulator. In one or more embodiments, the high speed pressure logger 120 may filter the indications of pressure received from the pressure sensors 116, 118 to remove noise and/or other perturbations from the indications unrelated to the pressure. The high speed pressure logger 120 may record the received indications of pressure at a periodic rate of 1000 hertz, 10000 hertz, 100000 hertz, or some other periodic rate. The high speed pressure logger 120 may store each pressure sample as an entry in a file that represents the given pressure value and the time associated with the pressure value. In one or more embodiments, the high speed pressure logger 120 may capture up to about 625,000 sample values per second. In another embodiment, however, a different sampling rate may be provided by the high speed pressure logger 120. In one or more embodiments, different types of pressure measurements may be stored by the high speed pressure logger 120 comprising, for example, pressure transients stored at a very high sampling rate as well as static pressure data sampled and recorded about every 7.5 seconds before and after opening of the fast opening flow control device 122.

In one or more embodiments, the high speed pressure logger 120 may comprise a ballistic pressure gauge. The ballistic pressure gauge may generally be configured to measure a plurality of pressure readings based on an input signal. For example, the opening of the fast opening flow control device 122 (e.g., a rupture disk or perforating charge) may trigger the initiation of the pressure readings at the time of the input signal or after a short delay. In one or more embodiments, the ballistic pressure gauge may allow for up to about 50,000 readings, 100,000 readings, 150,000 readings, 160,000 readings, or 200,000 readings, for example in a period ranging from about 0.001 seconds to about 1 second, about 0.01 seconds to about 0.75 seconds, or about 0.02 seconds to about 0.05 seconds. The ballistic pressure gauge may then be used to measure fluid flow of greater than about 50 ml/min, greater than about 75 ml/min, or greater than about 100 ml/min.

The scale 124 may comprise a receptacle to capture fluid overflow from the system 100, for example from a relief valve downstream of the fast opening flow control device 122. The receptacle is coupled to the scale 124 so that the weight of overflowed fluid may be weighed by the scale 124. In one or more embodiments, the receptacle may be releasably coupled to the scale 124, for example to promote draining fluid from the receptacle and cleaning the receptacle. The scale 124 may provide the indications of weight to the weight logger 126, and the weight logger 126 may filter the indications of weight received from the scale 124 to remove noise and/or other perturbations from the indications unrelated to weight. The weight logger 126 may record the received indications of weight at a periodic rate of 0.1 hertz, 0.5 hertz, 1 hertz, 2 hertz, 10 hertz, or some other periodic rate. The weight logger 126 may store each weight sample as an entry in a file that represents the given weight value and the time associated with the time value. In one or more embodiments, the weight logger 126 determines a tare weight output by the scale 124 when no fluid is contained by the receptacle coupled to the scale 124 and automatically compensates the weight indication received from the scale 124 based on the tare weight before creating records that are stored in the weight file.

In one or more embodiments, a computer 128 may receive pressure data from the pressure logger 120 and weight data from the weight logger 126. For example, the computer 128 may establish a wireless communication link or a wired communication link with the pressure logger 120 and download the pressure versus time data entries to a data store 130. The computer 128 may concurrently or at a different time establish a wireless communication link or a wired communication link with the weight logger 126 and download the weight versus time data entries to the data store 130. Alternatively, the pressure and weight data may be streamed to the computer 128 by the pressure logger 120 and the weight logger 126 substantially as the subject data is collected. The data store 130 may be a database, a flat file stored in memory or in secondary memory, a directory service Such as a lightweight directory access protocol (LDAP) storage, or some other form of data store. The computer 128 may process the data received from the loggers 120, 126 in a variety of ways and may process the data associated with different separate sets of data captured during different stages of rock core testing.

Figure 2:
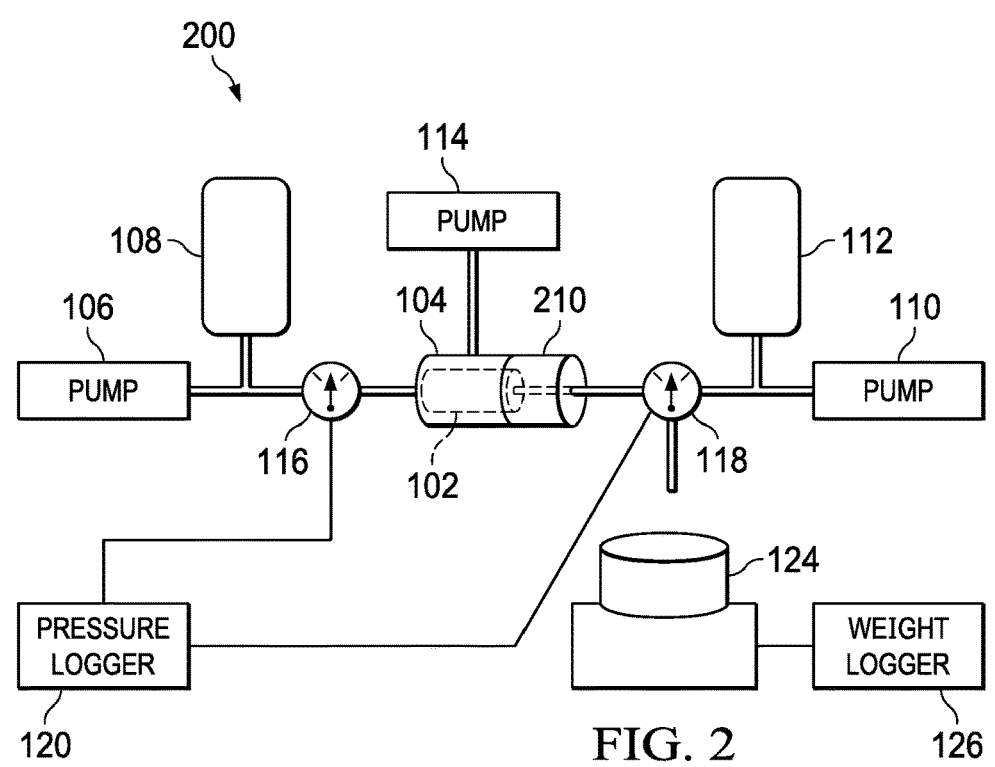

Turning now briefly to FIG. 2, a system 200 is described. System 200 is substantially similar to system 100 described above, but rather than the fast opening flow control device 122, system 200 includes a perforation assembly 210. Turning also briefly to FIG. 3, a system 300 is described. System 300 is substantially similar to system(s) 100, 200 described above, but rather than the fast opening flow control device 122 or perforation assembly 210, respectively, the system 300 includes a test gravel pack assembly 310. In one or more embodiments, system 100 is suitable for completing an initial stage of rock core testing, system 200 is suitable for completing a perforation stage of rock core testing, and system 300 is suitable for completing a gravel pack stage or rock core testing, as described in more detail hereinafter.

Figure 4A:
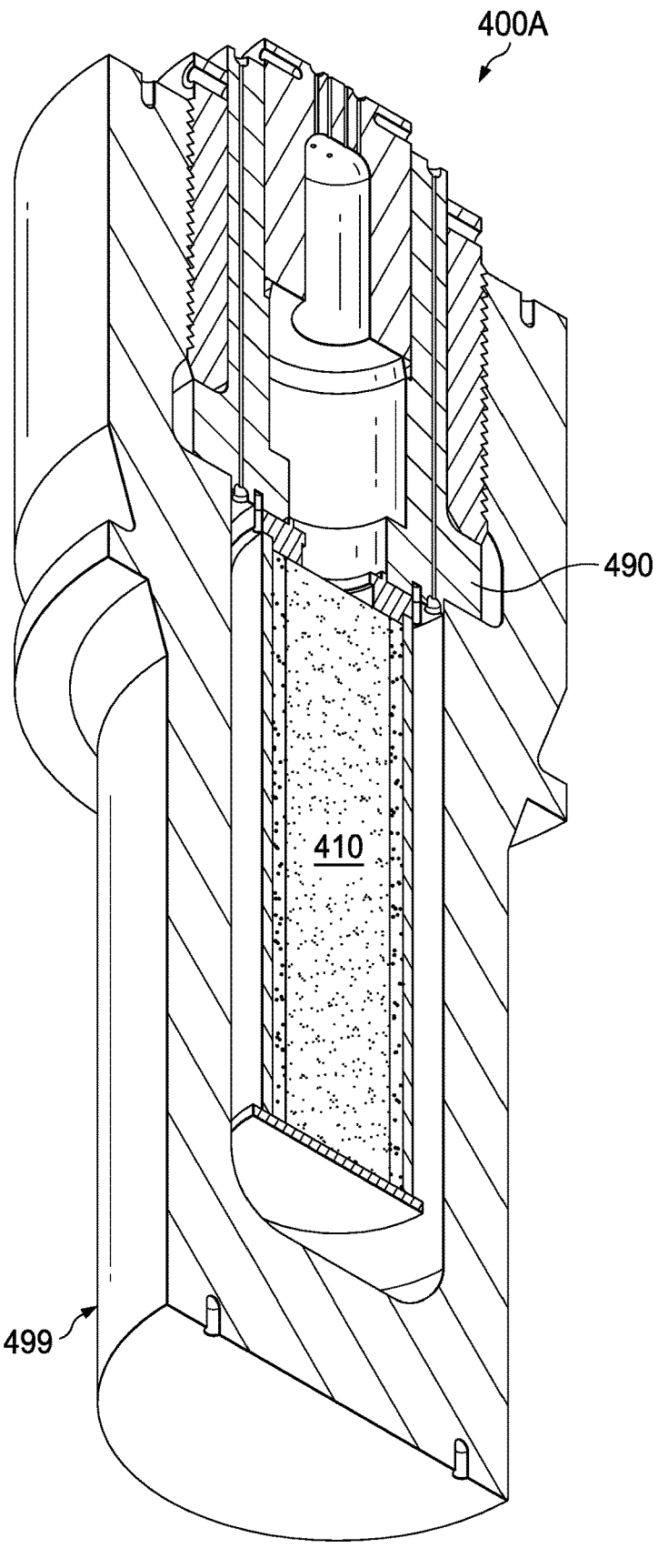
FIGS. 4A-4C illustrate various configurations of test gravel pack assemblies manufactured and designed according to embodiments of the disclosure.
Figure 4B:
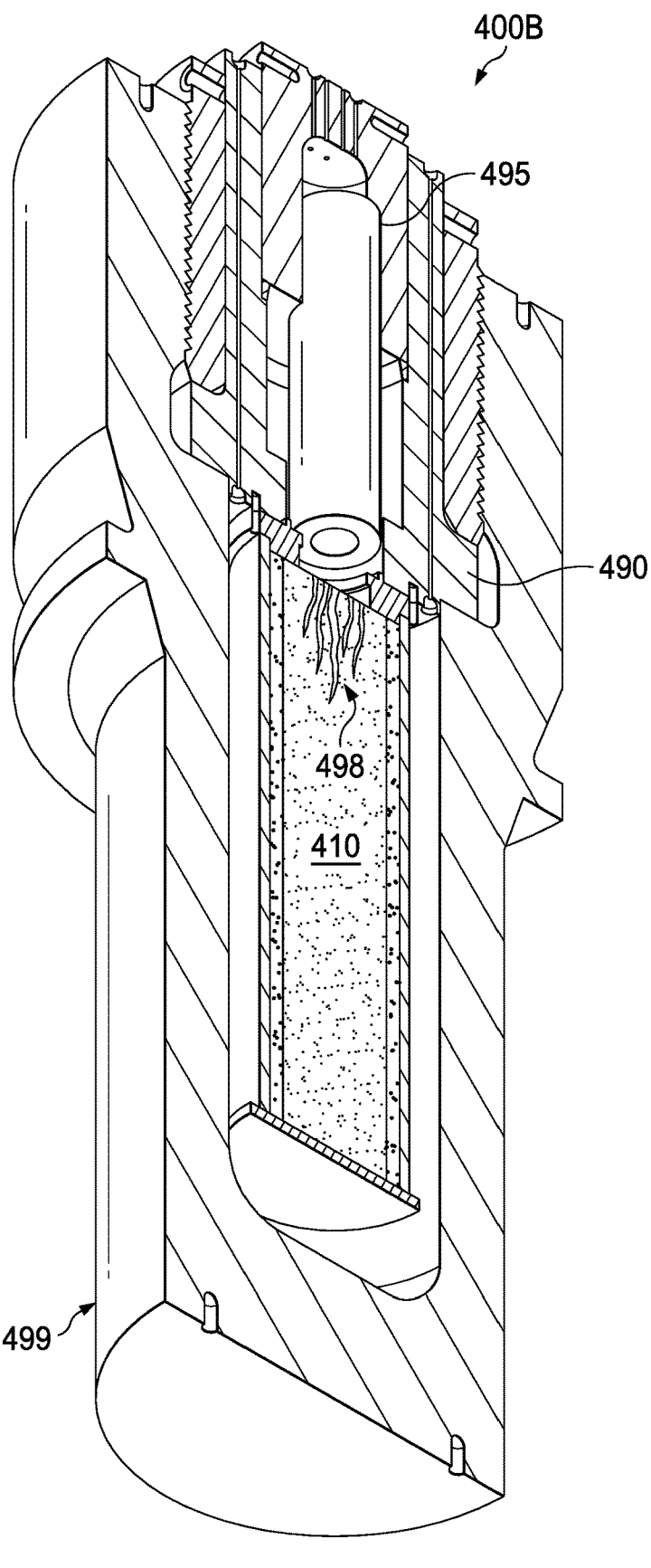
Figure 4C:
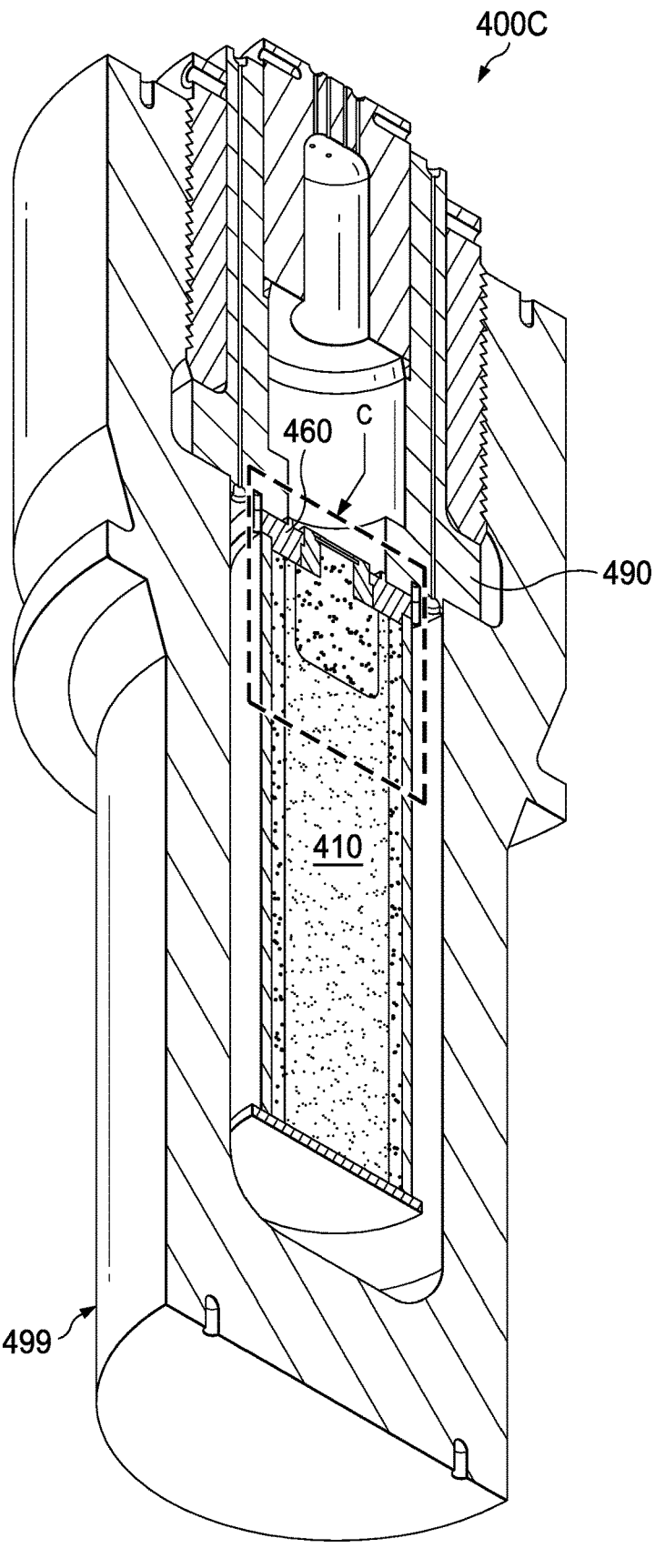

Turning to FIGS. 4A-4C, illustrated are various configurations of test gravel pack assemblies 400A, 400B, 400C manufactured and designed according to embodiments of the disclosure. The test gravel pack assembly 400A might be configured for use with the system 100 illustrated and described above with regard to FIG. 1, whereas the test gravel pack assembly 400B and test gravel pack assembly 400C might be configured for use with the systems 200, 300 illustrated and described above with regard to FIGS. 2 and 3, respectively. The test gravel pack assemblies 400A, 400B, 400C contain many similar, if not identical features. Accordingly, like reference numerals may be used to reference similar, if not identical, features.

With brief reference to FIG. 4A, the test gravel pack assembly 400A includes a rock core sample 410 coupled to a wellbore test structure 490, all of which is positioned within a pressure vessel 499. With brief reference to FIG. 4B, the test gravel pack assembly 400B additionally includes a perforation assembly 495, as might be used to form perforated areas 498 in the rock core sample 410. With brief reference to FIG. 4C, the test gravel pack assembly 400C additionally includes a test gravel pack assembly 460.

Figure 5:
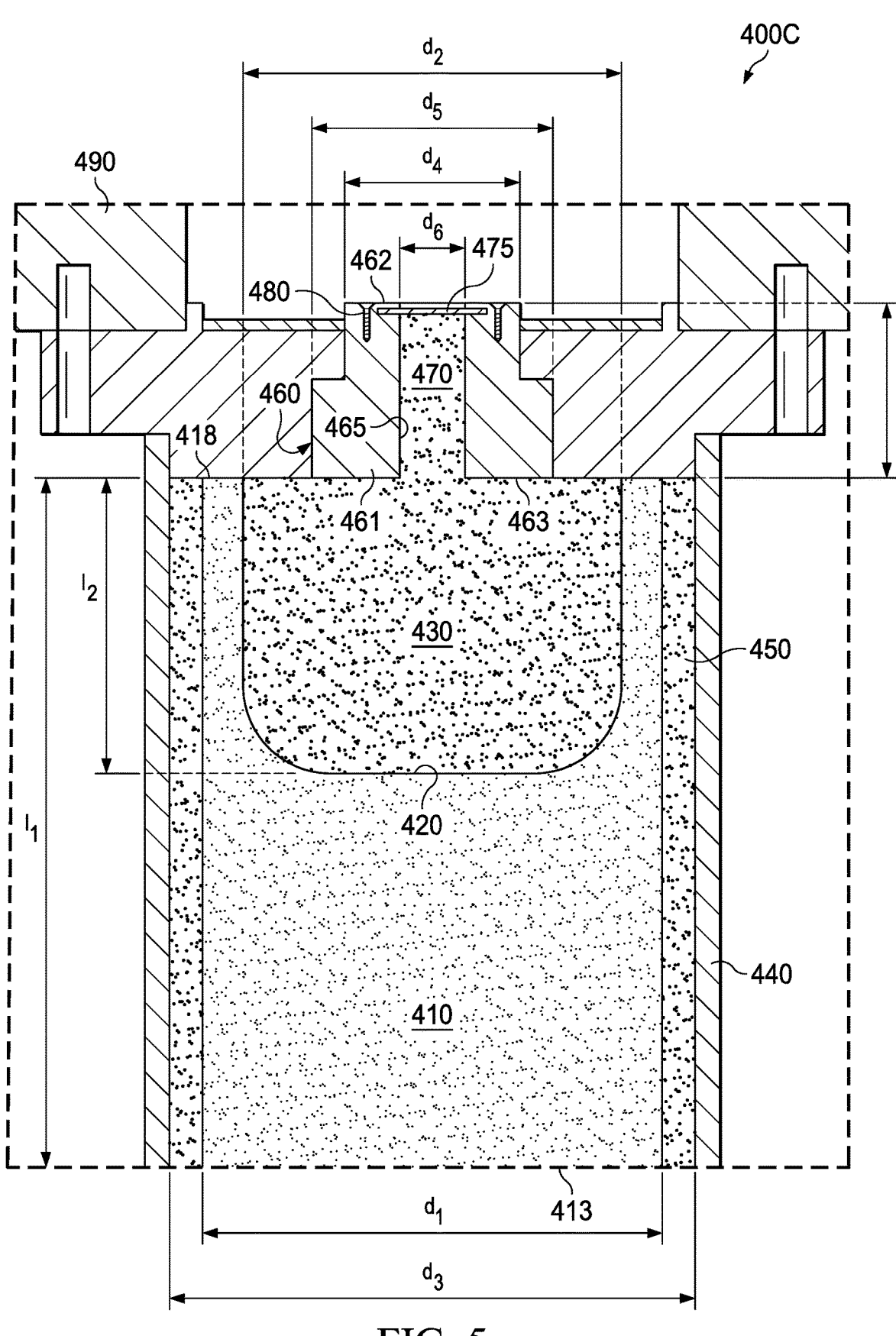
FIG. 5 illustrates a zoomed in view of the test gravel pack assembly, as taken from the dotted box C illustrated in FIG. 4C.

Turning now to FIG. 5, illustrated is zoomed in view of the test gravel pack assembly 400C, as taken from the dotted box C illustrated in FIG. 4C. The test gravel pack assembly 400C initially includes the rock core sample 410 having a pore axial end 413 and a wellbore facing end 418. The rock core sample 410 may comprise a field core or analog core, among other cores, and remain within the scope of the present disclosure The rock core sample 410, in accordance with the disclosure, will be of the type most likely to be found in the location of interest (e.g., where a customer might want to drill an oil/gas well). Many materials for the rock core sample 410 are within the scope of the disclosure, and thus the disclosure should not be limited to any specific material.

The rock core sample 410 may take on a variety of different sizes and remain within the purview of the disclosure. In one embodiment, however, the rock core sample 410 has a diameter ($d_1$) of at least about 18 centimeters (e.g., a little over 7 inches). In yet another embodiment, the rock core sample 410 has a diameter ($d_1$) of at least about 20.5 cm (e.g., a little over 8 inches), and in even another embodiment has a diameter ($d_1$) of at least about 21.5 cm (e.g., a little over 8.5 inches). It is believed that for big hole (e.g., larger shaped charge) systems, the rock core sample 410 benefits from having one of the larger diameters ($d_1$). In fact, if the diameter ($d_1$) of the rock core sample 410 is not sufficient, during the testing process (particularly after being subjected to the perforation process and being subjected to higher pressures) the rock core sample 410 may fail. The rock core sample 410 may additionally have different lengths ($l_1$) and remain within the scope of the disclosure. In one embodiment, however, the rock core sample 410 has a length ($l_1$) of at least about 36 cm (e.g., a little over 14 inches). In yet another embodiment, the rock core sample 410 has a length ($l_1$) of at least about 46 cm (e.g., a little over 18 inches).

The rock core sample 410 of FIG. 5 includes a perforated area 420 in a top portion thereof. The perforated area 420, as will be further discussed below, may be either a hole within the rock core sample 410, or alternatively an area of disturbed rock consisting of crushed and cracked pieces of the rock core sample 410. The perforated area 420 may also vary in size. In one test example, however, the perforated area 420 has a diameter ($d_2$) of at least about 7.5 cm (e.g., a little under about 3 inches). In another test example, however, the perforated area 420 has a diameter ($d_2$) of at least about 10 cm (e.g., a little under about 4 inches). In one test example the perforated area 420 extends into the rock core sample 410 by a distance ($l_2$) of at least about 6 cm (e.g., a little under about 2.5 inches). In another test example, however, the perforated area 420 extends into the rock core sample 410 by a distance ($l_2$) of at least about 7.5 cm (e.g., a little under about 3 inches).

Packed within the perforated area 420 in the test gravel pack assembly 400C of FIG. 5 is a proppant 430. The proppant 430 may comprise a typical gravel pack material as might be used in the oil/gas industry. The proppant 430 is configured to simulate the gravel pack that might exist downhole in an oil/gas well. Those skilled in the art understand the one or more different materials that the proppant 430 may comprise, including 20/40, 40/70, ceramic beads, etc.

The test gravel pack assembly 400C further includes a sleeve 440 (e.g., an impermeable sleeve, bladder, etc.) surrounding a longitudinal circumference of the rock core sample 410. The sleeve 440, in one embodiment, has an inner diameter ($d_3$) such that an annular space exists between the inner diameter ($d_3$) of the sleeve 440 and the outer diameter ($d_1$) of the rock core sample 410. In one particular embodiment, the inner diameter ($d_3$) is about 1.25 cm larger than the diameter ($d_1$) of the rock core sample 410. Accordingly, wherein the rock core sample 410 has a diameter ($d_1$) of about 21.5 cm, the sleeve 440 might have an inner diameter ($d_3$) of about 22.75 cm. Other embodiments exist, however, where no easily measurable space exists between the sleeve 440 and the rock core sample 410.

In the particular embodiment of FIG. 5, a second proppant 450 is placed within the annular space between the sleeve 440 and the rock core sample 410. The second proppant 450 may be a filler material that is spaced equidistance around the rock core sample 410. In at least one embodiment, rods are placed within the annular space such that the equidistance is created and the second proppant 450 can be placed therein. The second proppant 450 may be uniform beads, such as ceramic, bauxite or any other suitable material. In certain embodiments, the proppant 430 and the second proppant 450 comprise the same material, and in other embodiments the proppant 430 and the second proppant 450 comprise different materials.

A gravel pack simulation lab fixture 460 is positioned over the wellbore facing end 418 of the rock core sample 410, above the perforated area 420. The gravel pack simulation lab fixture 460 will most likely be made to match downhole casing, screen, standoffs, perf tunnel, through hole size, and any other relevant features. Generally speaking, each gravel pack simulation lab fixture 460 may differ from well to well that is being simulated.

The gravel pack simulation lab fixture 460, in accordance with the disclosure, includes a housing 461 having a first surface 462 and a second opposing surface 463. In accordance with one embodiment of the disclosure, the first and second opposing surfaces 462, 463 define a thickness (t) that simulates a desired downhole gravel pack thickness. In the illustrated embodiment shown, the first surface 462 has a first diameter ($d_4$) and the second opposing surface has a second greater diameter ($d_5$), for example as defined by the step feature in the housing 461.

In one or more embodiments, an opening 465 can extend entirely through the housing 461 from the first surface 462 to the second surface 463. The opening 465 may have a diameter ($d_6$) that simulates a desired downhole wellbore casing perforation diameter. Accordingly, the opening 465 may be tailored for the specific formation that it is to approximate. Additional proppant 470 may be located within the opening 465, e.g., packed therein. Those skilled in the art understand the one or more different materials that the proppant 470 may comprise. For example, the proppant 470 will most likely comprise the same material as the proppant 430, and may or may not comprise the same material as the second proppant 450.

In one or more embodiments, a proppant screen 475 is positioned over the proppant 470 and opening 465. The proppant screen 475, as depicted in the illustrated embodiment, is coupled proximate the first opposing surface 462, and is configured to hold the proppant 430 and proppant 470 in place. The proppant screen 475 may be configured to approximate a screen as might be used in a traditional oil/gas well. The proppant screen 475 may be a removable proppant screen that is maintained in place with two or more fasteners 480. For example, in the particular embodiment shown, four screws are used to maintain the proppant screen 475 in place.

Positioned over the gravel pack simulation lab fixture 460 is a wellbore test structure 490. In the illustrated embodiment of FIG. 5, the wellbore test structure 490 substantially surrounds the gravel pack simulation lab fixture 460. Moreover, the wellbore test structure 490, in the illustrated embodiment, includes a step feature that corresponds with the step feature in the gravel pack simulation lab fixture 460. The wellbore test structure 490, in this embodiment, is configured to approximate a traditional wellbore of an oil/gas well. The wellbore test structure 490 is additionally configured to subject the rock core sample 410 to similar wellbore pressures and temperatures as might be found downhole in a traditional oil/gas well.

FIGS. 6 and 7 illustrate a gravel pack simulation lab fixture 600 and a cap 700 manufactured and designed according to the disclosure. In this instance, the cap 700 would retain the proppant screen (not shown) over the opening in the gravel pack simulation lab fixture 600, and thus keep any proppant in a fixed position in the gravel pack simulation lab fixture 600.

A test gravel pack assembly, such as assemblies 400A, 400B, 400C, may be used to test the feasibility of a gravel pack assembly (e.g., 400C) at downhole conditions. The testing of the gravel pack assembly (e.g., 400B) would begin with acquiring a rock core sample (e.g., field core or analog core, 410). The rock core sample (e.g., 410) would then be assembled within an impermeable sleeve (e.g., 440). The rock core sample (e.g., 410) and the impermeable sleeve (e.g., 440) would be loaded into a vessel with a perforator (e.g., 495) planned for well perforation. The vessel would then be pressured to downhole conditions or agreed test conditions with customer. During tests, the vessel may be heated or may remain at ambient temperature. When the appropriate conditions are reached, a charge (e.g., shaped charge in one embodiment) is fired into the rock core sample (e.g., 410), thereby forming the perforated area (e.g., 498). The pressure is then relieved from the vessel, and the perforator (e.g., 495) is removed therefrom.

After removing the gravel pack assembly (e.g., 400B) from the vessel, one can physically place proppant (e.g., 430) into the area of lower density rock matrix created by perforation event and/or artificially create an open cavity to preferred requirements and fill the open cavity with proppant (e.g., 430). Thereafter, one can install the gravel pack simulation lab fixture (e.g., 460) on top of rock core sample (e.g., 410), and fill the opening (e.g., 465) in the gravel pack simulation lab fixture (e.g., 460) with proppant (e.g., by pouring from the top, 470). A screen (e.g., 475) may then be installed over the opening (e.g., 465), and the wellbore test structure (e.g., 490) may be installed there over.

With the test gravel pack assembly substantially complete, the test gravel pack assembly may be loaded back into the vessel and flow testing may be conducted. The flow testing may be conducted under high pressures (e.g., greater than 15K PSI) in the presence of one or more different types of fluids. In certain embodiments, the flow testing may be conducted under very high pressures (e.g., greater than 25K PSI), or in yet other embodiments conducted under extremely high pressures (e.g., greater than 40K PSI). A test gravel pack assembly according to the disclosure can handle each of high, very high and extremely high pressures, while providing useful data and remaining intact. In one embodiment, the flow testing is performed in the presence of odorless mineral spirits (OMS), or a light kerosene, among others.

Turning now to FIG. 8, one embodiment of a method of performing a rock core flow performance test 800 is described. In one or more embodiments, the method 800 may be employed to perform a transient pressure test. The method starts in a start step 805, and at step 810 one or more characteristics of a sample of subterranean rock are determined from the wellbore that is to be perforated are determined. The characteristics may be the density of the rock, the permeability of the rock, the type of rock, and other relevant characteristics. At step 815, based on the characteristics of the sample of subterranean rock, an outcrop rock is selected that suitably models the subterranean rock, and the sample of outcrop rock is shaped into a rock core sample having a suitable shape for flow testing. For example, step 815 could include lathing the rock core sample. It is understood that the rock core sample may be cut to any length and lathed to any diameter that is appropriate. The depth of the perforation expected to be created by the explosive charges of the perforation gun may be used to determine, at least in part, the length of the rock core sample.

At step 820, a high pressure flow test is performed on the rock core sample. This procedure is described in more detail above. In one or more embodiments, this high pressure flow test involves maintaining an overburden or confining pressure greater than 25000 PSI on the rock core sample. At step 825, a perforation assembly is coupled to a wellbore facing end of the rock core sample. At step 830, the perforation assembly is activated to perforate the rock core sample. At step 835, a high pressure flow test is performed on the perforated rock core sample. In one or more embodiments, this high pressure flow test involves maintaining an overburden or confining pressure greater than 25000 PSI on the rock core sample. The high pressure flow test of the perforated rock core sample may be conducted in substantially the same manner as step 820, which is again discussed above.

In a step 840, a test gravel pack assembly is coupled to the wellbore face end of the rock core sample. In a step 845, another high pressure flow test is performed on the rock core sample having the test gravel pack assembly coupled thereto. In some embodiments, steps 825, 830, and 840 are optional, and the method moves directly from step 820 to step 840.

The method continues with step 850, wherein a production ratio is determined based on data collected during the high pressure flow test performed on the unperforated rock core sample, during the optional high pressure flow test performed on the perforated rock core sample, and during the high pressure flow test performed with the test gravel pack assembly.

With brief reference back to FIGS. 1-3, the processing of step 850 may involve the computer 128 downloading data from the pressure logger 120 and/or from the weight logger 126 and analyzing this data. Alternatively, the data may be streamed from the pressure logger 120 and/or the weight logger 126 as the data is captured by these loggers 120, 126.

The computer 128 may further determine flow rates through the rock core sample at different times during the high pressure flow test of the unperforated rock core sample, during the high pressure flow test of the perforated rock core sample, and during the high pressure flow test of the perforated rock core sample in the presence of the gravel pack simulation lab fixture. The flow rates may be determined based on the weight samples downloaded from the weight logger 126 and based on compensating for compression effects of the fluid flowed in the rock core sample 102. For example, a table that defines fluid compression ratios at different pressures may be referenced by a compensation application executed by the computer 128. A fluid compression ratio may be proportional to the ratio of the volume of a unit mass of the subject fluid at a standard pressure such as atmospheric pressure to the volume of the unit mass of the subject fluid at an elevated pressure, such as at a pressure of 30,000 PSI. Alternatively, the fluid compression ratio may be proportional to the ratio of the volume of a unit mass of the subject fluid at an elevated pressure to the volume of the unit mass of the subject fluid at standard pressure.

The table may define the compression ratio of the subject fluid at each of 5000 PSI, 10000 PSI, 15000 PSI, 20000 PSI, 250000 PSI, 30000 PSI, 35000 PSI, 40000 PSI, 45000 PSI, 50000 PSI, 55000 PSI, and 60000 PSI. In another embodiment, the table may define more or fewer entries. The table may define different pressure indices, for example non-evenly spaced pressure indices. Rather than a table having entries of evenly spaced pressure indices, the table may have entries of evenly spaced compression ratios and corresponding pressure indices associated with each compression ratio. For values of pressure between the table entries, the compression ratio to apply may be linearly interpolated between the two closest pressure indices in the table or interpolated by another method.

Turning now briefly to FIG. 9, illustrated is a process flow 900, which expands steps 840, 850 and 860 into sub-steps. The process flow 900 begins by positioning a test gravel pack assembly (e.g., 400A) within a pressure vessel (e.g., 499) in a step 910. Thereafter, in a step 920, a pressure applied to the pore axial end (e.g., 413) of the rock core sample (e.g., 410) is increased to a first pressure, wherein the first pressure is greater than about 15,000 pounds per square inch (PSI). In a step 930, a pressure applied to the wellbore facing end (e.g., 418) of the rock core sample (e.g., 410) is increased to a second pressure greater than about 15,000 pounds per square inch (PSI). Steps 920 and 930 may be conducted in reverse order. In another example embodiment, steps 920 and 930 are conducted at the same time, and further their pressures are maintained substantially equal as the increase to the first pressure.

Thereafter, in a step 940, a pressure differential between the pressures applied to the pore axial end (e.g., 413) of the rock core sample (e.g., 410) and the wellbore facing end (e.g., 418) of the rock core sample (e.g., 410) may be created. This pressure differential induces fluid flow between the pore axial end (e.g., 413) and the wellbore facing end (e.g., 418) and through the opening (e.g., 465). For example, the pressure differential may be formed by reducing the pressure applied to one of the pore axial end (e.g., 413) or wellbore facing end (e.g., 418) of the rock core sample (e.g., 410) while maintaining the pressure applied to the other of the wellbore facing end (e.g., 418) or pore axial end (e.g., 413) of the rock core sample (e.g., 410). In one example embodiment, a fast opening flow control device (e.g., 122) is fluidly coupled to the wellbore facing end (e.g., 418) of the rock core sample (e.g., 410), and the fast opening flow control device (e.g., 122) is actuated to create the threshold pressure differential.

In a step 950, an overflow of a fluid that flows through the rock core sample (e.g., 410), the opening (e.g., 465), and the removable proppant screen (e.g., 475) is captured after creating the pressure differential, and in a step 960 the overflow of the fluid is weighed. With this information in hand, a first flow volume of the fluid through the rock core sample (e.g., 410) is determined based on a weight of the overflow of the fluid in a step 970.

Returning back to method 800, at step 855, the downhole perforation and/or gravel pack procedure may be adapted based upon the production ratio and/or based on other flow metrics determined based on the high pressure flow testing. For example, the gravel pack procedure may be adapted to provide better flow characteristics, including changing the thickness of the proppant, changing the type of proppant, etc. Additionally, the shaped charge may be adapted to diffuse explosive energy more broadly, the design of the liner of the shaped charge may be adapted, the tool body proximate to the shaped charge may be adapted.

Aspects disclosed herein include:

A. A test gravel pack assembly, including a housing having a first surface and a second opposing surface, the first surface and second opposing surface defining a thickness that simulates a desired downhole gravel pack thickness, an opening extending entirely through the housing from the first surface to the second opposing surface, the opening having a diameter that simulates a desired downhole wellbore casing perforation diameter, and a proppant screen coupled proximate the first surface and over the opening.

B. A rock core flow test system, the rock core flow test system including a pressure vessel, a test gravel pack assembly positioned within the pressure vessel, the test gravel pack assembly including a) a gravel pack simulation lab fixture, including, 1) a housing having first surface and a second opposing surface, the first surface and second opposing surface defining a thickness that simulates a desired downhole gravel pack thickness, 2) an opening extending entirely through the housing from the first surface to the second opposing surface, the opening having a diameter that simulates a desired downhole wellbore casing perforation diameter, and 3) a proppant screen coupled proximate the first surface and over the opening, b) a wellbore test structure surrounding the gravel pack simulation lab fixture, c) a rock core sample having a pore axial end and a wellbore facing end, and further wherein the wellbore facing end is in contact with the second opposing surface, the rock core flow test system further including a first high pressure accumulator coupled to the pressure vessel and in fluid communication with the pore axial end of the rock core sample, a second high pressure accumulator coupled to the pressure vessel and in fluid communication with the wellbore facing end of the rock core sample, and a pressure sensor coupled to the pressure vessel to measure changes in pressure to one or both of the first high pressure accumulator or the second high pressure accumulator.

C. A method of performing a rock core flow performance test, the method including positioning a test gravel pack assembly within a pressure vessel, the test gravel pack assembly including a) a gravel pack simulation lab fixture, the gravel pack simulation lab fixture including 1) a housing having a first surface and a second opposing surface, the first surface and the second opposing surface defining a thickness that simulates a desired downhole gravel pack thickness, 2) an opening extending entirely through the housing from the first surface to the second opposing surface, the opening having a diameter that simulates a desired downhole wellbore casing perforation diameter, and 3) a removable proppant screen coupled proximate the first surface and over the opening, b) a wellbore test structure surrounding the gravel pack simulation lab fixture, and c) a rock core sample having a pore axial end and a wellbore facing end, and further wherein the wellbore facing end of rock core sample is in contact with the second opposing surface, the method further including increasing a pressure applied to the pore axial end of the rock core sample to a first pressure, wherein the first pressure is greater than 15,000 pounds per square inch (PSI), increasing a pressure applied to the wellbore facing end of the rock core sample to a second pressure greater than 15,000 pounds per square inch (PSI), creating a pressure differential between the pressures applied to the pore axial end of the rock core sample and the wellbore facing end of the rock core sample, the pressure differential inducing fluid flow between the pore axial end and the wellbore facing end and through the opening, capturing an overflow of a fluid that flows through the rock core sample, the opening, and the removable proppant screen after the creating the pressure differential, weighing the overflow of the fluid, and determining a first flow volume of the fluid through the rock core sample based on a weight of the overflow of the fluid.

Aspects A, B, and C may have one or more of the following additional elements in combination: Element 1: wherein the proppant screen is a removable proppant screen. Element 2: wherein two or more fasteners couple the removable proppant screen to the first surface. Element 3: wherein the first surface has a first diameter, and the second opposing surface has a second greater diameter. Element 4: wherein the housing includes a step feature defining the first diameter and the second greater diameter. Element 5: wherein the housing, the opening and the proppant screen form at least a portion of a gravel pack simulation lab fixture, and further a wellbore test structure surrounding the gravel pack simulation lab fixture. Element 6: further including a rock core sample having a pore axial end and a wellbore facing end, and further wherein the wellbore facing end of the rock core sample is in contact with the second opposing surface. Element 7: wherein the rock core sample has a perforated area exposed to the opening, and further wherein proppant is packed within the perforated area and the opening, and held in place by the proppant screen. Element 8: wherein a sleeve surrounds a longitudinal circumference of the rock core sample. Element 9: wherein an annular space exists between the sleeve and the longitudinal circumference of the rock core sample, and further wherein a second proppant is located within the annular space. Element 10: wherein the proppant and the second proppant comprise a same material. Element 11: wherein the rock core sample has a perforated area in the wellbore facing end exposed to the opening, and further wherein proppant is packed within the perforated area and the opening, and held in place by the proppant screen. Element 12: wherein a sleeve surrounds a longitudinal circumference of the rock core sample thereby forming an annular space between the sleeve and the longitudinal circumference of the rock core sample, and further wherein a second proppant is located within the annular space. Element 13: further including a fast opening flow control device fluidly coupled to the wellbore facing end, wherein the fast opening flow control device is openable when a pressure differential across the fast opening flow control device exceeds a predefined threshold, and further wherein the pressure sensor is in fluid flow between the fast opening flow control device and the second high pressure accumulator. Element 14: wherein the rock core sample has a perforated area in the wellbore facing end exposed to the opening, and further including packing proppant within the perforated area and the opening prior to positioning the test gravel pack assembly within the pressure vessel, the proppant held in place by the proppant screen, and further wherein the pressure differential induces fluid flow between the pore axial end and the wellbore facing end and through the proppant in the perforated area and in the opening. Element 15: wherein the increasing a pressure applied to the pore axial end of the rock core sample and the increasing a pressure applied to the wellbore facing end of the rock core sample are maintained substantially equal as the pressures increases to the first pressure, and further wherein creating the pressure differential includes reducing the pressure applied to one of the pore axial end or wellbore facing end of the rock core sample while maintaining the pressure applied to the other of the wellbore facing end or pore axial end of the rock core sample. Element 16: wherein a fast opening flow control device is fluidly coupled to the wellbore facing end of the rock core sample. Element 17: wherein creating the pressure differential includes while maintaining the pressure applied to the pore axial end of the rock core sample at the first pressure, reducing the pressure applied to the wellbore facing end of the fast opening flow control device until the fast opening flow control device activates, wherein the fast opening flow control device activates in response to a threshold pressure differential across the fast opening flow control device.

Those skilled in the art to which this application relates will appreciate that other and further additions, deletions, substitutions and modifications may be made to the described embodiments.

What is claimed is:

1. A test gravel pack assembly, comprising:
a housing having a first surface and a second opposing surface, the first surface and second opposing surface defining a thickness that simulates a desired downhole gravel pack thickness, wherein the first surface has a first diameter, and the second opposing surface has a second greater diameter, and further wherein the housing includes a step feature defining the first diameter and the second greater diameter;
an opening extending entirely through the housing from the first surface to the second opposing surface, the opening having a diameter that simulates a desired downhole wellbore casing perforation diameter; and
a proppant screen coupled proximate the first surface and over the opening.

2. The test gravel pack assembly as recited in claim 1, wherein the proppant screen is a removable proppant screen.

3. The test gravel pack assembly as recited in claim 2, wherein two or more fasteners couple the removable proppant screen to the first surface.

4. The test gravel pack assembly as recited in claim 1, wherein the housing, the opening and the proppant screen form at least a portion of a gravel pack simulation lab fixture, and further a wellbore test structure surrounding the gravel pack simulation lab fixture.

5. The test gravel pack assembly as recited in claim 4, further including a rock core sample having a pore axial end and a wellbore facing end, and further wherein the wellbore facing end of the rock core sample is in contact with the second opposing surface.

6. The test gravel pack assembly as recited in claim 5, wherein the rock core sample has a perforated area exposed to the opening, and further wherein proppant is packed within the perforated area and the opening, and held in place by the proppant screen.

7. The test gravel pack assembly as recited in claim 6, wherein a sleeve surrounds a longitudinal circumference of the rock core sample.

8. The test gravel pack assembly as recited in claim 7, wherein an annular space exists between the sleeve and the longitudinal circumference of the rock core sample, and further wherein a second proppant is located within the annular space.

9. The test gravel pack assembly as recited in claim 8, wherein the proppant and the second proppant comprise a same material.

10. A rock core flow test system, comprising:
a pressure vessel;
a test gravel pack assembly positioned within the pressure vessel, the test gravel pack assembly including:
a gravel pack simulation lab fixture, including:
a housing having first surface and a second opposing surface, the first surface and second opposing surface defining a thickness that simulates a desired downhole gravel pack thickness;
an opening extending entirely through the housing from the first surface to the second opposing surface, the opening having a diameter that simulates a desired downhole wellbore casing perforation diameter; and
a proppant screen coupled proximate the first surface and over the opening;
a wellbore test structure surrounding the gravel pack simulation lab fixture; and
a rock core sample having a pore axial end and a wellbore facing end, and further wherein the wellbore facing end is in contact with the second opposing surface;
a first high pressure accumulator coupled to the pressure vessel and in fluid communication with the pore axial end of the rock core sample;
a second high pressure accumulator coupled to the pressure vessel and in fluid communication with the wellbore facing end of the rock core sample; and
a pressure sensor coupled to the pressure vessel to measure changes in pressure to one or both of the first high pressure accumulator or the second high pressure accumulator.

11. The rock core flow test system as recited in claim 10, wherein the rock core sample has a perforated area in the wellbore facing end exposed to the opening, and further wherein proppant is packed within the perforated area and the opening, and held in place by the proppant screen.

12. The rock core flow test system as recited in claim 11, wherein a sleeve surrounds a longitudinal circumference of the rock core sample thereby forming an annular space between the sleeve and the longitudinal circumference of the rock core sample, and further wherein a second proppant is located within the annular space.

13. The rock core flow test system as recited in claim 10, further including a fast opening flow control device fluidly coupled to the wellbore facing end, wherein the fast opening flow control device is openable when a pressure differential across the fast opening flow control device exceeds a predefined threshold, and further wherein the pressure sensor is in fluid flow between the fast opening flow control device and the second high pressure accumulator.

14. A method of performing a rock core flow performance test, comprising:
positioning a test gravel pack assembly within a pressure vessel, the test gravel pack assembly including:
a gravel pack simulation lab fixture, including:

a housing having a first surface and a second opposing surface, the first surface and the second opposing surface defining a thickness that simulates a desired downhole gravel pack thickness;

an opening extending entirely through the housing from the first surface to the second opposing surface, the opening having a diameter that simulates a desired downhole wellbore casing perforation diameter; and a removable proppant screen coupled proximate the first surface and over the opening;

a wellbore test structure surrounding the gravel pack simulation lab fixture; and a rock core sample having a pore axial end and a wellbore facing end, and further wherein the wellbore facing end of rock core sample is in contact with the second opposing surface;

increasing a pressure applied to the pore axial end of the rock core sample to a first pressure, wherein the first pressure is greater than 15,000 pounds per square inch (PSI);

increasing a pressure applied to the wellbore facing end of the rock core sample to a second pressure greater than 15,000 pounds per square inch (PSI);

creating a pressure differential between the pressures applied to the pore axial end of the rock core sample and the wellbore facing end of the rock core sample, the pressure differential inducing fluid flow between the pore axial end and the wellbore facing end and through the opening;

capturing an overflow of a fluid that flows through the rock core sample, the opening, and the removable proppant screen after the creating the pressure differential;

weighing the overflow of the fluid; and determining a first flow volume of the fluid through the rock core sample based on a weight of the overflow of the fluid.

15. The method as recited in claim 14, wherein the rock core sample has a perforated area in the wellbore facing end exposed to the opening, and further including packing proppant within the perforated area and the opening prior to positioning the test gravel pack assembly within the pressure vessel, the proppant held in place by the proppant screen, and further wherein the pressure differential induces fluid flow between the pore axial end and the wellbore facing end and through the proppant in the perforated area and in the opening.

16. The method as recited in claim 14, wherein the increasing a pressure applied to the pore axial end of the rock core sample and the increasing a pressure applied to the wellbore facing end of the rock core sample are maintained substantially equal as the pressures increases to the first pressure, and further wherein creating the pressure differential includes reducing the pressure applied to one of the pore axial end or wellbore facing end of the rock core sample while maintaining the pressure applied to the other of the wellbore facing end or pore axial end of the rock core sample.

17. The method as recited in claim 16, wherein a fast opening flow control device is fluidly coupled to the wellbore facing end of the rock core sample.

18. The method as recited in claim 17, wherein creating the pressure differential includes while maintaining the pressure applied to the pore axial end of the rock core sample at the first pressure, reducing the pressure applied to the wellbore facing end of the fast opening flow control device until the fast opening flow control device activates, wherein the fast opening flow control device activates in response to a threshold pressure differential across the fast opening flow control device.

19. A test gravel pack assembly, comprising:

a housing having a first surface and a second opposing surface, the first surface and second opposing surface defining a thickness that simulates a desired downhole gravel pack thickness;

an opening extending entirely through the housing from the first surface to the second opposing surface, the opening having a diameter that simulates a desired downhole wellbore casing perforation diameter;

a proppant screen coupled proximate the first surface and over the opening; and a rock core sample having a pore axial end and a wellbore facing end, and further wherein the wellbore facing end of the rock core sample is in contact with the second opposing surface.

* * * * *